United States Patent
Wehnes et al.

(10) Patent No.: US 10,376,230 B2
(45) Date of Patent: Aug. 13, 2019

(54) OBTAINING BREAST DENSITY MEASUREMENTS AND CLASSIFICATIONS

(71) Applicant: iCAD, Inc., Nashua, NH (US)

(72) Inventors: Jeffrey C. Wehnes, Richardson, TX (US); Arunkumar Gururajan, Dallas, TX (US); James Monaco, Frisco, TX (US); Ronald Larcom, Frisco, TX (US); James H. Pike, Carrollton, TX (US)

(73) Assignee: iCad, Inc., Nashua, NH (US)

( * ) Notice: Subject to any disclaimer, the term of this patent is extended or adjusted under 35 U.S.C. 154(b) by 0 days.

(21) Appl. No.: 15/035,743

(22) PCT Filed: Nov. 10, 2014

(86) PCT No.: PCT/US2014/064876
§ 371 (c)(1),
(2) Date: May 10, 2016

(87) PCT Pub. No.: WO2015/077076
PCT Pub. Date: May 28, 2015

(65) Prior Publication Data
US 2016/0256126 A1 Sep. 8, 2016

Related U.S. Application Data

(60) Provisional application No. 61/906,279, filed on Nov. 19, 2013, provisional application No. 61/969,626, filed on Mar. 24, 2014.

(51) Int. Cl.
*G06T 7/00* (2017.01)
*A61B 6/00* (2006.01)
*G06T 7/11* (2017.01)

(52) U.S. Cl.
CPC ............ *A61B 6/5217* (2013.01); *A61B 6/502* (2013.01); *G06T 7/0012* (2013.01); *G06T 7/11* (2017.01);
(Continued)

(58) Field of Classification Search
None
See application file for complete search history.

(56) References Cited

U.S. PATENT DOCUMENTS 8,315,446 B2    11/2012   Raundahl et al.
8,675,933 B2    3/2014    Wehnes et al.
(Continued)

OTHER PUBLICATIONS

Strickland, Robin N., and Hee Il Hahn. "Wavelet transforms for detecting microcalcifications in mammograms." IEEE Transactions on Medical Imaging 15.2 (1996): 218-229.*
(Continued)

*Primary Examiner* — Vu Le
*Assistant Examiner* — Tracy Mangialaschi
(74) *Attorney, Agent, or Firm* — Loginov & Associates, PLLC; William A. Loginov

(57) ABSTRACT

Breast density measurements are used to perform Breast Imaging Reporting and Data System (BI-RADS) classification during breast cancer screenings. The accuracy of breast density measurements can be improved by quantitatively processing digital mammographic images. For example, breast segmentation may be performed on a mammographic image to isolate the breast tissue from the background and pectoralis tissue, while a breast thickness adjustment may be performed to compensate for decreased tissue thickness near the skin line of the breast. In some instances, BI-RADS density categorization may consider the degree to which dense tissue is dispersed throughout the breast. A breast density dispersion parameter can also be obtained using (Continued)

quantitative techniques, thereby providing objective BI-RADS classifications that are less susceptible to human error.

14 Claims, 8 Drawing Sheets

(52) U.S. Cl.
CPC .............. *G06T 2207/10004* (2013.01); *G06T 2207/10116* (2013.01); *G06T 2207/30068* (2013.01)

(56) References Cited

U.S. PATENT DOCUMENTS

| | | | |
|---|---|---|---|
| 8,675,934 | B2 | 3/2014 | Wehnes et al. |
| 8,855,388 | B2 | 10/2014 | Wehnes et al. |
| 8,923,594 | B2 | 12/2014 | Wehnes et al. |
| 9,076,197 | B2 | 7/2015 | Wehnes |
| 9,256,799 | B2 | 2/2016 | Wehnes et al. |
| 2005/0152589 | A1 | 7/2005 | Wehnes et al. |
| 2010/0046814 | A1* | 2/2010 | Dewaele ............. G06T 7/0012 382/128 |
| 2010/0124364 | A1 | 5/2010 | Huo et al. |
| 2011/0026791 | A1* | 2/2011 | Collins ................ G06K 9/62 382/131 |
| 2011/0150313 | A1* | 6/2011 | Su ....................... G06T 7/0012 382/132 |
| 2011/0280465 | A1 | 11/2011 | Wehnes et al. |
| 2013/0202165 | A1 | 8/2013 | Wehnes et al. |
| 2013/0272595 | A1 | 10/2013 | Heine et al. |

OTHER PUBLICATIONS

Chang, Ruey-Feng, et al. "Three comparative approaches for breast density estimation in digital and screen film mammograms." Engineering in Medicine and Biology Society, 2006. EMBS'06. 28th Annual International Conference of the IEEE. IEEE, 2006.*

Glide-Hurst, Carri K., Neb Duric, and Peter Littrup. "A new method for quantitative analysis of mammographic density." Medical physics 34.11 (2007): 4491-4498.*

Otsu, "A Threshold Selection Method From Gray-Level Histograms", "IEEE Transactions on Systems, Man, and Cybernetics", Jan. 1, 1979, pp. 62-66, vol. SMC-9, No. 1, Publisher: IEEE, Published in: US.

Rauh, et al., "Percent Mammographic Density and Dense Area as Risk Factors for Breast Cancer", Aug. 1, 2012, pp. 727-733, vol. 72, No. 8, Publisher: Geburtshilfe Frauenheilkunde, Published in: DE.

Brake, et al, "Single and Multiscale Detection of Masses in Digital Mammograms", "IEEE Transactions on Medical Imaging", Jul. 1, 1999, pp. 628-639, vol. 18, No. 7, Publisher: IEEE, Published in: US.

* cited by examiner

OBTAINING BREAST DENSITY MEASUREMENTS AND CLASSIFICATIONS

This patent application claims priority to U.S. Provisional Application No. 61/906,279, filed on Nov. 11, 2013 and entitled "System and Methods for Obtaining Breast Density Measurements from Digital Mammograms," and U.S. Provisional Application No. 61/969,626, filed on Mar. 24, 2014 and entitled "Systems and Methods for Obtaining Breast Density Classifications based on Breast Density Ratios and Dense Tissue Dispersion," both of which are hereby incorporated by reference herein as if reproduced in their entireties.

TECHNICAL FIELD

The present invention relates to medical imaging, and, in particular embodiments, to systems and methods for obtaining breast density measurements and breast density classifications.

BACKGROUND

Digital mammograms are commonly used to diagnose breast cancer in women. One important consideration in mammographic screenings is breast density, which generally corresponds to the ratio of the area of glandular/connective tissue to the total breast area. More specifically, breast density is considered a risk factor for breast cancer development, as women exhibiting relatively high amounts of dense tissue are thought to be four to five times more likely to develop breast cancer than women with average (or comparatively lower) amounts of dense tissue. Moreover, breast tissue may potentially mask cancerous lesions because dense fibro-glandular tissue exhibits similar x-ray attenuation properties as cancerous masses/calcifications. As such, techniques for accurately measuring breast density and/or identifying dense breast tissue are desired.

SUMMARY OF THE INVENTION

Technical advantages are generally achieved, by embodiments of this disclosure which describe systems and methods for obtaining breast density measurements and breast density classifications.

In accordance with an embodiment, a method for breast density computation is provided. In this example, the method includes performing breast segmentation on a mammographic image to obtain breast and pectoral muscle segmentation maps, performing breast thickness correction on the mammographic image to obtain a flattened breast image, and computing a breast density measurement in accordance with the breast and pectoral muscle segmentation maps and the flattened breast image. An apparatus for performing this method is also provided.

In accordance with another embodiment, a method for breast density classification is provided. In this example, the method comprises computing a breast density ratio and a dispersion measurement value for a mammographic image. The breast density ratio corresponds to a percentage of dense breast tissue in a breast depicted by the mammographic image, and the dispersion measurement value corresponds to a distribution of the dense tissue in the breast. The method further comprises assigning a breast density classification to the mammographic image in accordance with the breast density ratio and the dispersion measurement value. An apparatus for performing this method is also provided.

BRIEF DESCRIPTION OF THE DRAWINGS

For a more complete understanding of the present invention, and the advantages thereof, reference is now made to the following descriptions taken in conjunction with the accompanying drawing, in which.

DETAILED DESCRIPTION OF ILLUSTRATIVE EMBODIMENTS

Figure 1:
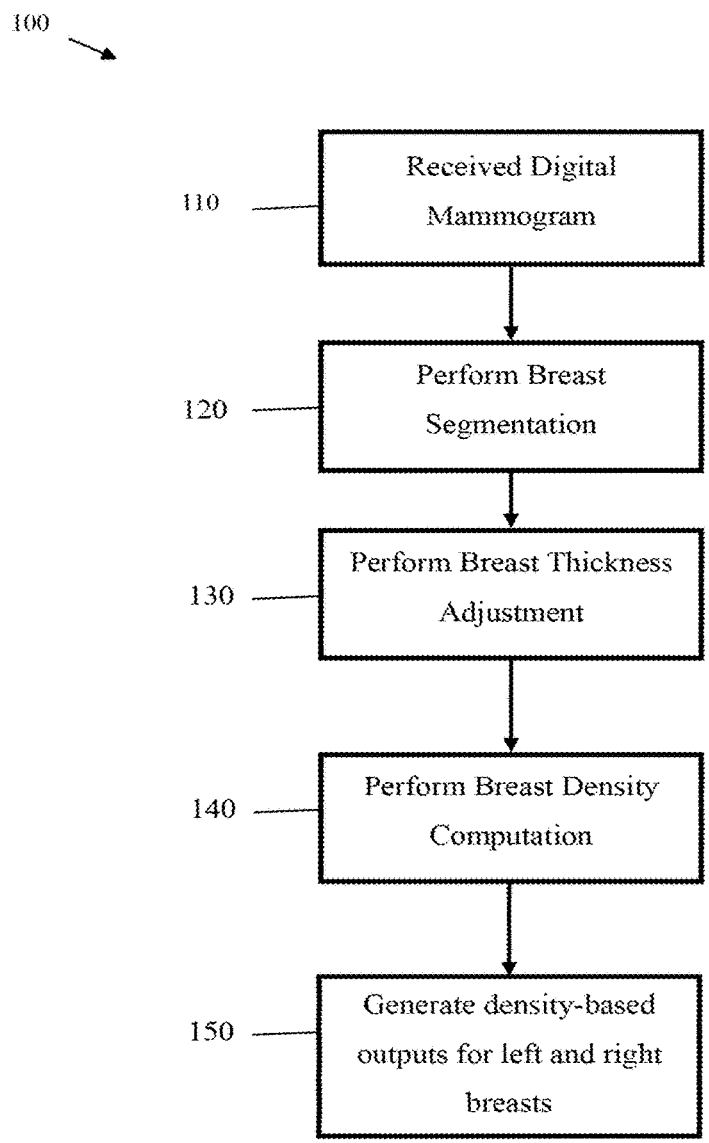
FIG. 1 illustrates a flow chart of an embodiment method for processing digital mammographic images to obtain a breast density measurement.

The making and using of the presently disclosed embodiments are discussed in detail below. It should be appreciated, however, that the present invention provides many applicable inventive concepts that can be embodied in a wide variety of specific contexts. The specific embodiments discussed are merely illustrative of specific ways to make and use the invention, and do not limit the scope of the invention.

Quantitative assessments of mammographic density typically rely on tissue classifications defined by the Breast Imaging Reporting and Data System (BI-RADS) density categorizations, which include (a) predominantly or almost entirely fatty, (b) scattered fibroglandular densities, (c) heterogeneously dense, and (d) extremely dense. One conventional technique for assigning BI-RADS density categories relies on a radiologist's visual examination of the mammogram, which tends to lead to coarse/imprecise measurements that are highly subjective. Another conventional technique for assigning BI-RADS density categories relies on calibration data provided by the imaging device, such as a radiation dose and/or an exposure period used to generate the mammographic image. This conventional technique may be unsuitable in some situations, as many electromagnetic radiation (x-ray) imaging devices are incapable of providing calibration data. Moreover, even in situations where radiation-dose/exposure-period information is available, the accuracy of that information may be dependent on various factors, such as the age/condition of the x-ray imaging device as well as how recently the x-ray imaging device was calibrated. Hence, conventional techniques that classify breast tissue based on calibration data may in many instances produce unreliable/inaccurate breast density measurements. As such, quantitative techniques for generating objective, accurate, and precise measurements of breast density are desired.

Aspects of this disclosure provide quantitative techniques for obtaining breast density measurements from digital mammographic images. Embodiment quantitative techniques may perform various pre-processing steps prior to computing breast density. For instance, breast segmentation may be performed prior to breast density computation in order to isolate (i) breast from the background, and (ii) breast tissue from pectoralis tissue. Additionally, breast thickness adjustment may be performed prior to breast density computation in order to compensate for decreased tissue thickness near the skin line. Embodiment breast density computation techniques may produce estimates of breast density for each breast. These estimates may include a total area of the breast in square centimeters ($cm^2$), an area of the breast covered by dense tissue in square centimeters ($cm^2$), and a breast density measurement (e.g., percentage of breast area composed of dense tissue). Additionally, techniques provided herein may also determine a BI-RADS breast density category solely from the digital mammographic images and without relying on the physics of the X-ray imaging device (e.g., radiation dosage, exposure period, etc.).

FIG. 1 illustrates a flow chart of a method 100 for processing a digital mammogram to obtain a breast density measurement, as may be performed by a breast density engine. As shown, the method 100 begins with step 110, where the breast density engine receives a digital mammogram. The digital mammogram may be obtained from any source, e.g., medical imaging devices, electronic databases, etc. Next, the method 100 proceeds to step 120, where the breast density engine performs breast segmentation on the digital mammogram to identify the portion of the image representing the breast. Breast segmentation techniques are described in greater detail by other portions of this disclosure, such as the descriptions accompanying FIG. 2 (below).

Thereafter, the method 100 proceeds to step 130, where the breast density engine performs breast thickness correction on the digital mammogram. Breast thickness correction may adjust the image such that grayscale values near the edge of the breast are more similar to grayscale values near the interior of the breast. Breast thickness correction may compensate for decreased thickness near the skin line, which typically results in fatty tissue near the skin-line to have lower intensities as compared to fatty tissue located near the chest wall. In some embodiments, breast thickness correction is achieved by computing an estimated level of underlying fatty tissue as a function of the distance from the breast boundary, and then subtracting the estimated level of underlying fatty tissue from the original image to obtain a flattened image. An embodiment breast thickness correction technique is described in U.S. Patent Application Publication 2013/0202165, which is hereby incorporated by reference herein as if reproduced in its entirety. In some applications, breast thickness correction techniques may assume that an optimal (or near optimal) breast boundary has been computed. Subsequently, the method 100 proceeds to step 140, where the breast density engine performs breast density computation based on various inputs. Inputs for the breast density computation may include original images, thickness corrected images, and breast and pectoral muscle segmentation maps. Breast density computation techniques are described in greater detail by other portions of this disclosure, such as the descriptions accompanying FIG. 6. Finally, the method 100 proceeds to step 150, where the breast density engine generates density-based outputs for the left and right breasts.

Breast segmentation techniques analyze digital mammographic images to identify the portion of the image representing the breast. Breast segmentation may generate a pixel map identifying each pixel as belonging to one of three classes: (i) breast tissue; (ii) pectoral tissue; or (iii) other/background (e.g., pixels that represent neither breast nor pectoral tissue). Breast segmentation may also approximate one or more lines and/or points pertaining to boundaries and/or regions of the breast. For instance, breast segmentation may approximate the breast curve as a set of points lying along the skin line delineating the extent of the breast. Breast segmentation may also approximate a pectoral (pec) line delineating the outer edge of the pectoralis muscle. The pectoral line may be approximated using linear regression techniques, and may be modeled as a "best-fit" line representing the outer edge of the pectoralis muscle. Breast segmentation may also approximate the nipple point based upon information from the breast and pectoral boundaries.

In some embodiments, breast segmentation is performed independently on each view of an original mammographic image, including the left craniocaudal view (LCC), the left mediolateral oblique view (LMLO), the right craniocaudal view (RCC), and the right mediolateral oblique view (RMLO). An embodiment breast segmentation algorithm may use the standard left side orientation for location descriptions. For example, the torso may be described as being located along the image's left side with the breast extending to the right. Embodiment breast segmentation techniques include various steps, such as breast skin line estimation to estimate an outline of the breast curve, pectoral muscle segmentation to obtain a boundary between breast tissue and pectoralis muscle, and post-processing to detect the nipple region and create the breast segmentation map.

Figure 2:
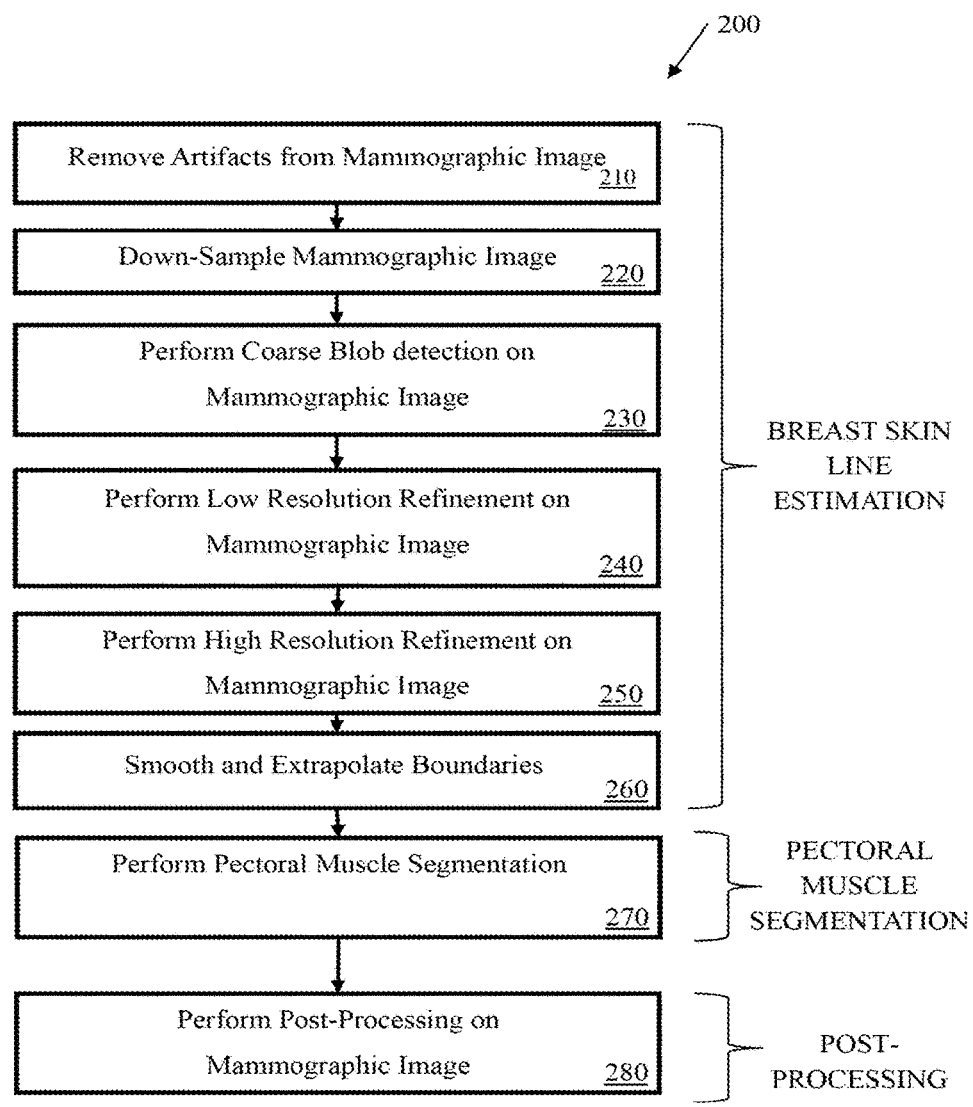
FIG. 2 illustrates a flow chart of an embodiment method for performing breast segmentation on a digital mammographic image.

FIG. 2 illustrates a flow chart of a method 200 for performing breast segmentation on a view in a mammographic image. As shown, the method 200 includes the steps 210-280, with steps 210-260 being directed at breast skin line estimation, step 270 being directed at breast pectoral muscle segmentation, and step 280 being directed at post-processing. Briefly, breast skin line estimation (e.g., steps 210-260) outputs an estimation of the breast curve (e.g., an outline of the breast), while breast pectoral muscle segmentation (e.g., step 270) outputs an estimated line separating breast tissue from the pectoral muscle. Post-processing (e.g., step 280) includes nipple detection and breast map creation.

As shown, the method 200 begins with step 210, where the breast density engine removes artifacts from the mammographic image to obtain an artifact free sub-image of the original image for further processing. Notably, digital mammograms frequently contain artifact pixels not representative of tissue or air. Common examples of digital artifacts are dark or bright bars aligned with the image edges. An algorithm can be applied to identify each class of artifacts using an appropriate image metric, such as a constant image value or a presence of consistently strong edge responses along an image column or row. The algorithm then truncates the image by selecting a sub-window free of artifacts for further processing. Thereafter, the method 200 proceeds to step 220, where the breast density engine down-samples the mammographic image to a lower resolution to allow for faster processing of the image.

Subsequently, the method 200 proceeds to step 230, where the breast density engine performs coarse blob detection on the mammographic image. In this step, an initial coarse segmentation is performed by selecting an optimal intensity based threshold. The selected threshold divides the histogram of image pixels into background pixels (low intensity) and foreground pixels (high intensity pixels representing tissue, tags, etc.). Due to the low noise of digital mammograms, the background variance (sensor noise) is generally quite low compared to the foreground variance (sensor noise+variation of tissue). Accordingly, a threshold selection algorithm may bias the threshold towards a smaller variance in the background class. For example, weighted intra-class variance can be reduced and/or minimized by biasing the algorithm in the manner described by Institute of Electrical and Electronics Engineers (IEEE) Transactions on Systems, Man and Cybernetics publication, vol. 9, no. 1 (1970) article entitled "A threshold selection method from Gray-Level Histograms," which is hereby incorporated herein by reference as if reproduced in its entirety. Applying the selected threshold to the input image creates an image of binary blobs. Standard morphological operations can be applied to these blobs to separate the breast blob from potentially impinging blobs, which result from image artifacts (e.g., tags, etc.). The breast density engine may then select blobs that are most likely to represent the breast based on size and location. In some examples, the right edge of the blob is used as the initial breast boundary.

Next, the method 200 proceeds to step 240, where the breast density engine performs low resolution refinement on the mammographic image. In this step, the breast density engine may use the initial breast boundary's curvature properties to truncate that boundary to obtain an estimated outline of the breast tissue. Truncation may include removing boundary points which lie along the abdomen or upper arm. The boundary may be adjusted by evaluating image intensity characteristics of points sampled along a vector normal to the boundary at each boundary point. Each boundary point can be adjusted along its normal vector to the outermost point (e.g., the point furthest away from the breast) with a slope exceeding a threshold derived from global image properties. The slope may meet certain point-to-point consistency and/or inner minimum intensity requirements.

Notably, when remote processing is used, the refined mammographic images may be compressed and transmitted to a remote server following low-resolution refinement. Portions of the image outside of the refined boundary curve (e.g., plus a margin of error) can be zeroed out to allow more efficient image compression. Image compression can be performed using any error-free compression technique. The compressed image can be transmitted to a remote server for further processing.

Thereafter, the method 200 proceeds to step 250, where the breast density engine performs high resolution refinement on the mammographic image. More specifically, the refined boundary from step 240 is transformed to the coordinate space of the original image down sampled to an intermediate resolution between the original mammogram resolution and the coarse resolution in step 220. The boundary points are again refined with a radial search at this higher resolution. The image second derivative is sampled along each radial vector by calculating the local image Hessian and projecting it along the curve normal direction. The radial refinement then selects local second derivative maxima along the radial search vector which is most consistent with neighboring refinements. High resolution refinement can be performed after compression and/or transmission of the image in embodiments where remote processing is utilized.

Subsequently, the method 200 proceeds to step 260, where the breast density engine smooths and extrapolates boundaries in the mammographic image. In this step, the boundary may be processed to correct refinement errors by adjusting points to remove high curvature along the boundary path. In addition, the boundary can be extrapolated to cover off-image regions, as may occur in the case of large or poorly positioned breasts. Extrapolation may ensure that the breast boundary and the left side of the image enclose the breast tissue region. The boundary can also be extended to the left side of the image for cranio-caudal views or the top and left side of the image for medio-lateral oblique views.

After completing the breast skin line estimation, the method 200 proceeds to step 270, where pectoral muscle segmentation is performed to distinguish the pectoral muscle from breast tissue in the mammographic image. Pectoral muscle segmentation techniques are described in greater detail by other portions of this disclosure, such as the descriptions accompanying FIG. 3 (below). After completing pectoral muscle segmentation, the method 200 proceeds to step 280, where post-processing is performed to detect the nipples and create a segmentation map. Post-processing techniques may select a nipple point as the point of the detected breast boundary furthest from the pectoralis edge (or the left side of the image in the cranio-caudal views). Furthermore, post-processing techniques may use the breast boundary and the pectoralis boundary to create a segmentation map. Pixels between the breast boundary and image left are labeled as breast tissue, with the exception of pixels between the left side of the image and edge of the pectoralis muscle, which are labeled as pectoralis tissue. Any remaining pixels are labeled as background. Background may include any non-breast/pectoralis tissue, such as upper arm and abdomen tissue.

Pectoral muscle segmentation allows pectoral tissue to be distinguished from breast tissue in mammographic images. In some embodiments, a pectoral muscle segmentation algorithm is applied to each mediolateral oblique view in order to identify the boundary between the pectoralis muscle and the remainder of the breast tissue. Inputs for the pectoral muscle segmentation algorithm may include a digital image of the breast and a binary map separating the breast from the background. Pectoral muscle segmentation may generally be achieved by extracting lines indicating intensity edges from the image using a line detection algorithm, discarding extracted lines whose characteristics (e.g. length, orientation, position) are inconsistent with a pectoralis boundary, and forming a final continuous boundary by selecting lines (e.g., from the remaining extracted lines) that are most likely to correspond to the pectoralis boundary. Notably, the pectoralis segmentation algorithm described herein may also be used to detect skin folds in a mammogram.

Figure 3:
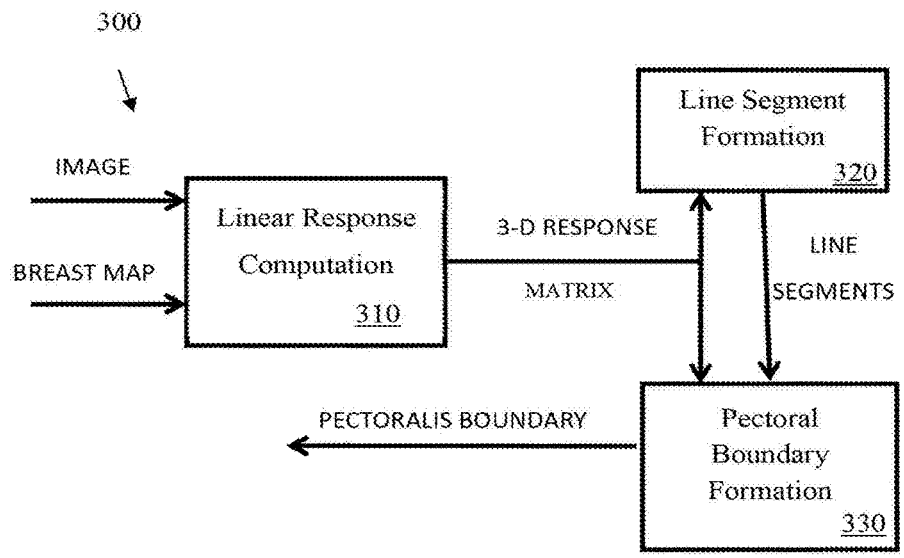
FIG. 3 illustrates a diagram of an embodiment procedure for performing pectoral muscle segmentation on a digital mammographic image.
Figure 4:
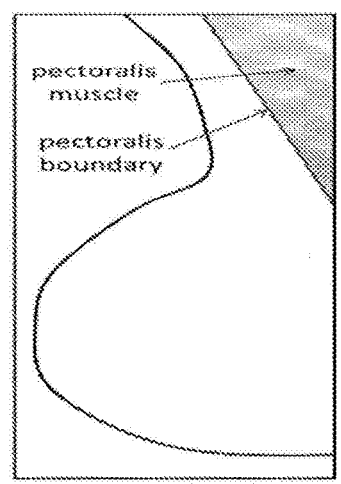
FIG. 4 illustrates a diagram demonstrating a pectoralis muscle being isolated from breast tissue.

FIG. 3 illustrates a block diagram of a pectoral muscle segmentation procedure 300 configured to isolate the pectoralis muscle from the breast tissue, as shown by the diagram in FIG. 4. As shown, the pectoral muscle segmentation procedure 300 includes a linear response computation step 310, a line segment formation step 320, and a pectoral boundary formation step 330.

Figure 5:
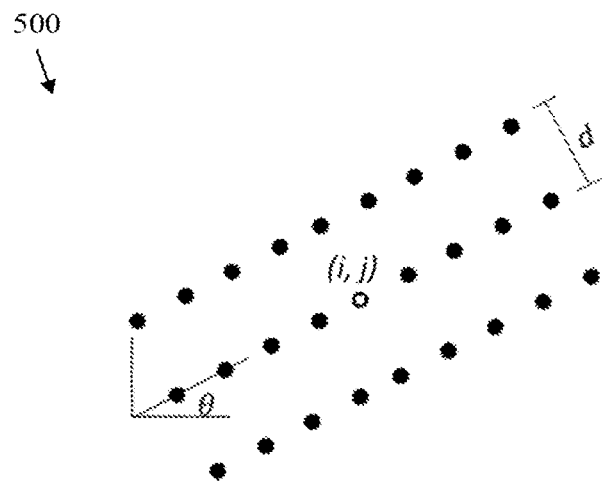
FIG. 5 illustrates a diagram of interpolation points for determining statistical information for second derivatives relating to digital mammographic images.

The linear response computation step 310 detects linear structures in an image. Linear structures are detected by measuring the linear edge response at every pixel, transforming the measured responses into a binary map of edge pixels, and linking the binary map of edge pixels to form edge lines. In some embodiments, a linear edge response finding algorithm is applied to detect linear responses during pectoral muscle segmentation. The linear edge response finding algorithm may compute probabilities that an edge at angle θ passes through a given pixel (i,j). Probabilities may be calculated at each pixel and each possible angle (e.g., each angle in a discrete set of angles) to create a 3D matrix. This result is derived from a 5D matrix whose values indicate the probability that a line of length L, scale S, and θ passes through image pixel (i, j). The general approach follows. For each image point (i, j), a 3×L rectangular array of points rotated by θ is linearly interpolated from the image. The vertical spacing d between points is a function of the scale is demonstrated in FIG. 5, which illustrates a grid of interpolation points used to determine the mean and standard deviation of second derivative along a linear segment center about pixel (i,j). Using the interpolated values, the second derivate at each point in the middle row (which contains L samples) is calculated by subtracting the intensity of the inner point from the average of the intensities of the outer two points. Thereafter, the signal strength (e.g. using the mean, median, or order statistic) and signal consistency (e.g. using the standard deviation, median absolute deviation, or coefficient of variation) are determined using the second derivatives (e.g., L second derivatives), yielding two 5D matrices. A single 5D matrix is then obtained from the strength and consistency matrices. The single 5D matrix indicates the probability that a line of length L, scale S, and angle θ passes through image pixel (i, j). A parametric density estimation technique is used to determine the cumulative distribution functions (CDFs) of the strength and consistency matrices. These CDFs are determined separately for each length and scale across all pixels and angles. Using these CDFs, it is possible to calculate the probability that a given pixel of a specified length and scale would produce a strength (or consistency) whose value is greater than the measured value. The probabilities for the strength and consistency may be calculated independently and then multiplied together. In this manner, the two 5D matrices of strengths and consistencies are converted into a single 5D matrix of probabilities. Finally, the 5D matrix is condensed to a 3D matrix by combining the response across scales and lengths. The final 3D response matrix is passed to the next step in the boundary finding process.

The line segment formation step 320 creates a list of edge lines using the 3D response matrix produced by the linear response computation step 310. Initially, the line segment formation step 320 may identify the local maxima in the response matrix, which may include the maxima in all three dimensions, thereby creating a binary matrix that indicates the locations of edge pixels. Notably, edge pixels whose associated probabilities are below a threshold may be eliminated. Thereafter, the line segment formation step 320 may link the edge points to form lines. In doing so, the 3D binary map may first be thinned to ensure that a given edge pixel is not adjacent to more than two other edge pixels, and then edge pixels that are adjacent in 3D-space may be connected to form line segments. After formation, the resulting line segments may be connected based on various factors, such as the distance between their endpoints, the angle between the line segments, and probability values at the endpoints.

The pectoral boundary formation step 330 produces a continuous boundary separating the pectoral muscle from the remainder of the breast tissue. The boundary is produced using the line segments and the 3D response matrix produced by the line segment formation step 320 and the linear response computation step 310, respectively. In some embodiments, the pectoral boundary is computed using one or more regression algorithms. For instance a least squares regression may first be performed on all possible combinations of line segments (e.g., combinations of one and two lines) to obtain a second order polynomial corresponding to the line points. Thereafter, the second order polynomial may be adjusted (e.g., re-fit) by performing a weighted least squares regression on all the points in the binary 3D matrix of edge points. After adjusting the second order polynomial, the resulting polynomial is assessed by measuring the weighted spatial distance between the edge pixels and the polynomial, the difference between the angles of the edge pixels (which is known from the 3D response matrix) to the angle of the polynomial (at the closest point), and the difference between the angles of the edge pixels and the mean expected angle of a typical pectoralis boundary. After the polynomial boundary is calculated for each possible combination of line segments, it is determined whether the boundary should be discarded based on its spatial location, average angle, average curvature, the area of resulting pectoral muscle, and the area of the remaining breast tissue. After removing all unreasonable boundaries, the boundary with the greatest goodness-of-fit is retained as the final pectoral boundary.

Figure 6:
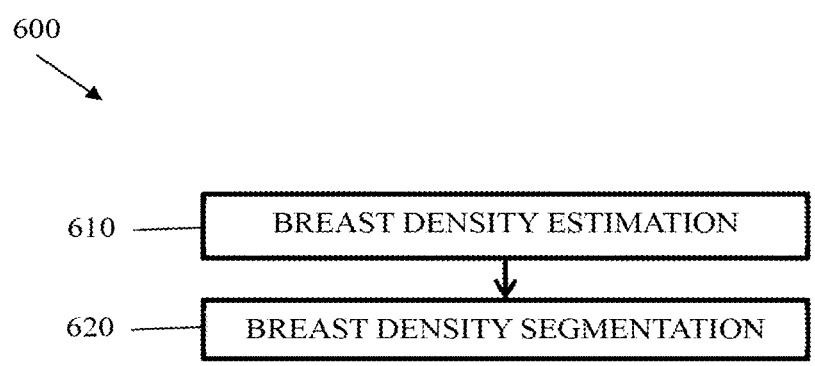
FIG. 6 illustrates a flow chart of an embodiment method for performing breast density computation for a digital mammographic image.

Breast density may be computed using the original images (e.g., LCC/LMLO/RCC/RMLO views), the thickness corrected images for each of the views, and the breast and pectoral muscle segmentation maps for each of the views. FIG. 6 illustrates a method 600 for performing breast density computation. As shown, the method 600 begins at step 610, where breast density estimation is performed to achieve coarse dense tissue segmentation. Thereafter, the method 600 proceeds to step 620, where breast density segmentation is performed to achieve fine dense tissue segmentation. In this step, the coarse segmentation output is further refined using complementary image intensity information at a higher resolution.

Figure 7:
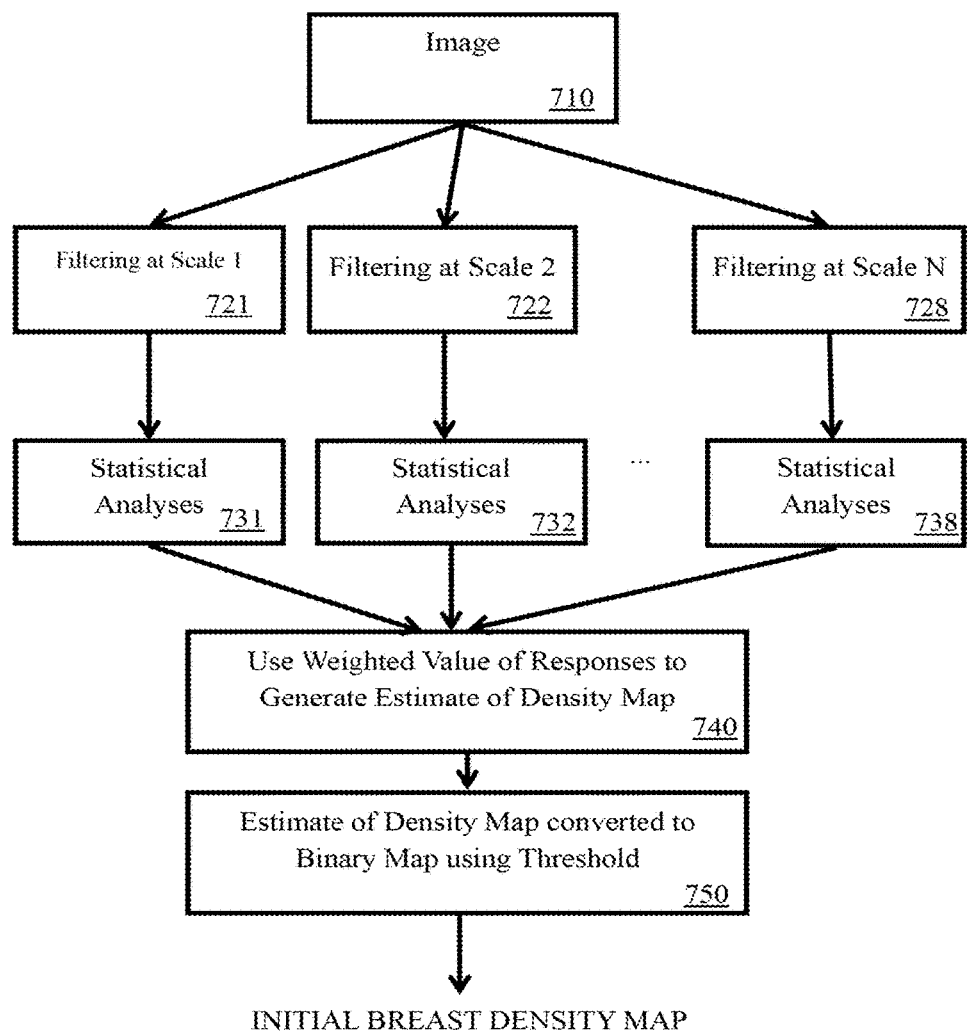
FIG. 7 illustrates a flow chart of an embodiment method for performing breast density estimation for a digital mammographic image.

Breast density segmentation may include multi-scale texture analysis in order to ascertain an initial estimate of the dense tissue in the breast. FIG. 7 illustrates a method 700 for achieving breast density estimation. As shown, the method 700 begins with step 710, where the image is received. Thereafter, the method 700 proceeds to steps 721-728, where the image is filtered using N different scales to obtain N filtered outputs. The multi-scale filtering may enhance scale-specific physical characteristics of the image. The image can be filtered in any domain. In an embodiment, the image is filtered in the spatial domain using, for example, spatial-domain convolutional filters. In another embodiment, the image is filtered in the frequency domain using a Fourier transformation with tuned band-pass filters. In yet another embodiment, the image is filtered jointly in the spatial-frequency domain using a wavelet filter-bank. Notably, filtering is not limited to a particular instantiation of the aforementioned techniques. For example, the image could be filtered using multiple classes of wavelets (or all classes of possible wavelets), including orthogonal wavelets (e.g. Haar, Daubechies etc.), non-orthogonal wavelets (e.g. Gabor, log-Gabor etc.), or combinations thereof.

Thereafter, the method 700 proceeds to steps 731-738, where the filtered outputs are statistically analyzed in order to agglomerate the signal within a specified region-of-interest (ROI). This ROI may be a function of the scale at which the output image was generated. Thereafter, the method 700 proceeds to step 740, where one or more weighted values corresponding to the statistical response images are used to generate an initial continuous-valued estimate of the density map. In one embodiment, the weighted value(s) include ratios between two statistical response images. In another embodiment, the weighted value(s) include a classifier obtained by combining two or more response images. In one example, the weighted value(s) include a linear classifier obtained by taking a linear combination of two or more response images. In other examples, the weighted value(s) can include a Bayes classifier, a quadratic classifier, or any other type of classifier. Subsequently, the method 700 proceeds to step 750, where the density map is converted to a binary map using a selected threshold. The threshold may be selected such that the dense regions (corresponding to the parenchymal tissue) and the fatty regions are assigned distinctive labels. The output of step 750 may be an initial breast density map.

Figure 8:
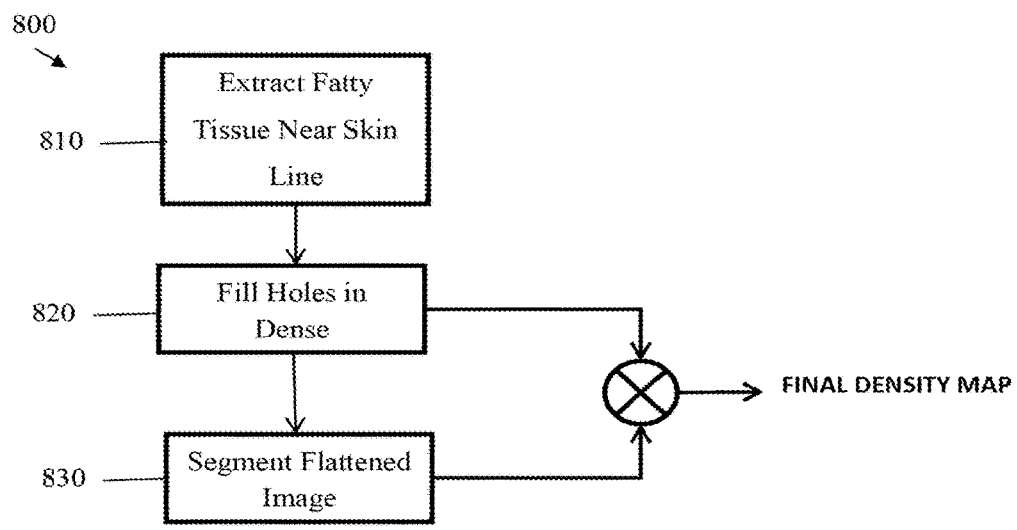
FIG. 8 illustrates a flow chart of an embodiment method for performing breast density segmentation on a digital mammographic image.

Breast density segmentation further refines the initial breast density map using complementary image intensity information at a higher resolution. FIG. 8 illustrates a flowchart of a method 800 for achieving breast density segmentation. As shown, the method 800 begins at step 810, where fatty tissue near the skin-line is extracted. Fatty tissue extraction can be achieved using a clustering technique that segregates the image into clusters with minimal intra-class variance while simultaneously maximizing inter-class variance.

Subsequently, the method 800 proceeds to step 820, where holes in the dense tissue are filled. A transformation can be applied to the pixel intensities, after which the transformed pixel intensities in the dense region are modeled probabilistically using a parametric distribution. The parameters of the distribution are specified using information from the initial density map. Using this distribution, a likelihood map is generated for all the pixels within the breast region. The likelihood map may assume high values for extremely dense regions and low values for other regions in the breast. The likelihood map is then segmented using a two-level optimal thresholding technique to produce a segmentation map of the extremely dense areas. Finally, the extremely dense areas are added to the existing density map to form an initial density map.

Next, the method 800 proceeds to step 830, where segmentation of the flattened breast image is performed. More specifically, fatty pixels are extracted from the flattened breast image using the refined breast density map as reference. Statistics of the fatty region are also extracted. Notably, the flattened breast image may include bright artifacts near the breast edge, particularly in cases where the breast segmentation is somewhat inaccurate. To mitigate the impact of these artifacts on the fatty region statistics, the extracted fatty pixels are passed through an outlier detection process prior to computing the region statistics. Following this, the threshold for segmenting the flattened image is selected as a function of the region-statistics, as well as the initial estimate of the percent breast density. This process yields a flattened-image breast density map, which is consequently combined with the initial density map to yield the final breast density map. Various techniques can be used to combine the refined density map and the flattened breast image. In one embodiment, the final breast density map is obtained by taking a logical AND of the refined density map and the flattened breast image.

In some embodiments, breast density outputs are generated for each of the four views using the final breast density map. More specifically, the final breast density map is used to compute a dense area for each view, a breast area for each view, and a percent breast density for each view. The dense area is calculated by summing all the "white" or dense pixels in the final breast density map, and multiplying it by the square of the pixel resolution (centimeters) to yield the dense area in square centimeters. The breast area is calculated by summing all the pixels in the breast segmentation map, and multiplying it by the square of the pixel resolution (centimeters) to yield the breast area in square centimeters. The percent breast density is calculated by dividing the dense area by the breast area and multiplying the ratio by 100.

Thereafter, each of the measurements is averaged across the craniocaudal and mediolateral oblique views to obtain the dense areas, breast areas, and percent breast density for each breast. These per-side averaged measurements are reported by the system. Additionally, the maximum percent breast density across the right and left breasts is taken and mapped to a BI-RADS breast density category.

Figure 9:
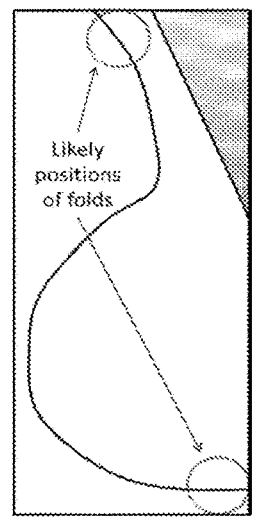
FIG. 9 illustrates a diagram of fold intersections in a mammographic image.

Aspects of this disclosure can be used to detect skin folds in mammographic images. More specifically, skin often becomes folded during a mammogram, resulting in a crease. The creases (or folds) may appear as long lines or ridges of high intensity in the mammographic image, which can create intensity profiles when intersecting with other prominent linear structures such as the breast boundary or other folds. These intensity profiles can be mistaken for dense-like structures (e.g., mass-like structures, cancer-like structures, and/or other high density areas), and therefore it is desirable to detect the folds. Fold intersections usually occur in the areas where the skin line meets the edge of the image, as illustrated in FIG. 9. Aspects of this disclosure provide a fold detection algorithm to identify regions containing fold intersections. Inputs to the algorithm include a digital image of the breast and a binary map separating the breast from the background. The algorithm may extract lines indicative of strong intensity edges in the image using the line detection procedure disclosed above. The algorithm may also identify points of intersection between lines, and flag intersection points occurring near both the skin line and image edges as being potentially problematic folds, e.g., folds that may exhibit intensity profiles that are mistaken for dense-like structures.

Some techniques provided by this disclosure are described as being performed by a breast density engine. As discussed herein, breast density engines may include hardware components, software components, or combinations thereof that are individually or collectively configured to process digital mammograms to obtain breast density measurements. In some examples, breast density engines may be incorporated within or piggybacked on medical imaging devices used to generate or analyze digital mammograms. In other examples, breast density engines may be standalone devices. Digital mammograms may refer to any electronic file or collection of files used to store medical imaging information related to human breasts. Further, while many aspects of this disclosure are discussed in the context of mammograms, techniques described herein are applicable to other medical imaging disciplines as well. As such, techniques described herein are not limited to mammograms unless otherwise stated.

U.S. Provisional Patent Application 61/906,279 provides quantitative breast density classification techniques that classify breasts based on the ratio (or percentage) of breast density found in mammograms. These quantitative breast density classification techniques simulate the manner in which radiologists classify breast density using the BI-RADS standard. Recently, the American College of Radiology (ACR) updated the BI-RADS standard to consider the distribution of dense tissue throughout the breast in addition to the ratio of dense-tissue in the breast. For example, breasts may be assigned a lower density classification when the dense tissue is relatively well distributed throughout the breast. Conversely, breasts may be assigned a higher density classification if the dense tissue is poorly distributed throughout the breast, as may occur when much of the dense tissue is localized to a specific area of the breast.

Figure 10:
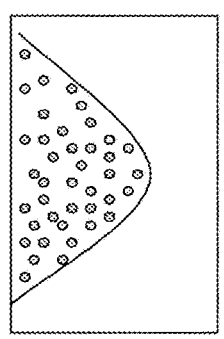
FIG. 10 illustrates a diagram of dense tissue distributions in a mammographic image.
Figure 11:
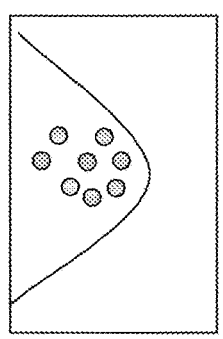
FIG. 11 illustrates a diagram of dense tissue distributions in another mammographic image.
Figure 12:
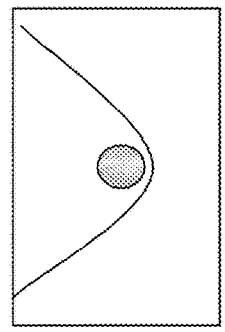
FIG. 12 illustrates a diagram of dense tissue distributions in yet another mammographic image.

Aspects of this disclosure provide a dispersion assessment step that can be used in conjunction with the quantitative breast density classification techniques provided by U.S. Provisional patent application 61/906,279 to comply with the updated BI-RADS classification standard. In an embodiment, the dispersion assessment step measures the degree to which dense tissue is dispersed throughout the breast. This may be achieved by computing the dispersion measurement based on a breast density map, e.g., refined density map, final density map, etc., with higher dispersion measurement values corresponding to greater distributions of dense tissue throughout the breast. FIGS. 10-12 illustrate diagrams of mammographic images 1000, 1100, 1200 of breasts having different ratios of dense tissue and/or different distributions of dense tissue. The gray circles represent regions of dense tissue. Dense tissue within the same circle may be considered minimally dispersed, while dense tissue in different circles may be considered maximally dispersed. The terms minimally dispersed and maximally dispersed are used loosely to describe the relative dispersion of dense tissue, and should not be interpreted literally for the purpose of limiting the scope of this disclosure, or the scope of the claimed invention.

The breasts depicted by the mammographic images 1000, 1100 have approximately the same ratio of dense tissue, with the dense tissue in the breast depicted by the mammographic image 1000 being more distributed than the dense tissue in the breast depicted by the mammographic image 1100. The breast depicted by the mammographic image 1200 has a lower ratio of dense tissue than the breasts depicted by the mammographic images 1000, 1100, with the dense tissue in the breast depicted by the mammographic image 1200 being less distributed than the dense tissue in the breast depicted by the mammographic images 1000, 1100.

Figure 13:
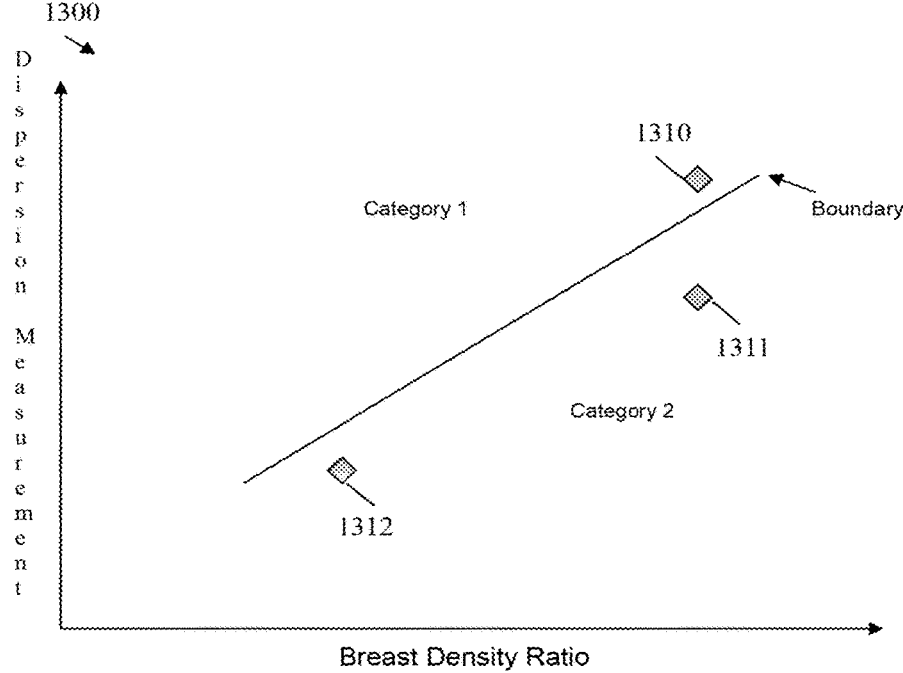
FIG. 13 illustrates a graph of a breast boundary between two Breast Imaging Reporting and Data System (BI-RADS) classification categories.

The dispersion measurement may be used in conjunction with the density ratio to perform BI-RADS classification. FIG. 13 illustrates a graph 1300 of a breast boundary between two BI-RADS classification categories, namely: Category 1; and Category 2. Category 1 may correspond to any of the lowest three BI-RADS classification (e.g., BI-RADS-a, BI-RADS-b, BI-RADS-c), while Category 2 corresponds to the next highest BI-RADS classification relative to Category 1. For example, if Category 1 corresponds to BI-RADS-c, then Category 2 corresponds to BI-RADS-d. As shown, the x-axis of the graph 1300 corresponds to breast density ratios, while the y-axis of the graph 1300 corresponds to dispersion measurement values. The dispersion measurement values may correspond to the distribution of dense tissue throughout the breast, with higher dispersion measurement values indicating higher distributions of dense tissue throughout the breast. The graph 1300 depicts three points 1310, 1311, and 1312 corresponding to the mammograms 1000, 1100, and 1200 (respectively). Despite having approximately the same density ratios, the breast depicted by the mammogram 1000 is assigned a lower BI-RADS classification than the breast depicted by the mammogram 1100 due to the breast depicted by the mammogram 1000 being assigned a higher dispersion measurement than the breast depicted by the mammogram 1100. Moreover, the breast depicted by the mammogram 1000 is assigned a lower BI-RADS classification than the breast depicted by the mammogram 1200 by virtue of their disparate dense tissue distributions.

Various aspects of this disclosure can be used for computer aided detection as well as breast density. For example, the embodiment breast segmentation algorithm can be used for computer aided detection.

Figure 14:
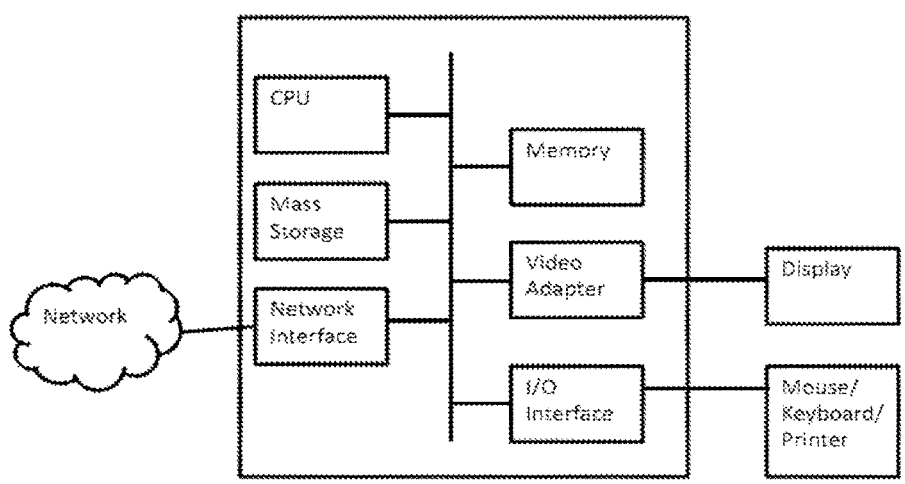
FIG. 14 illustrates a computing platform that may be used for performing embodiment methods described herein.

FIG. 14 is a block diagram of a processing system that may be used for implementing the devices and methods disclosed herein. Specific devices may utilize all of the components shown, or only a subset of the components, and levels of integration may vary from device to device. Furthermore, a device may contain multiple instances of a component, such as multiple processing units, processors, memories, transmitters, receivers, etc. The processing system may comprise a processing unit equipped with one or more input/output devices, such as a speaker, microphone, mouse, touchscreen, keypad, keyboard, printer, display, and the like. The processing unit may include a central processing unit (CPU), memory, a mass storage device, a video adapter, and an I/O interface connected to a bus.

The bus may be one or more of any type of several bus architectures including a memory bus or memory controller, a peripheral bus, video bus, or the like. The CPU may comprise any type of electronic data processor. The memory may comprise any type of non-transitory system memory such as static random access memory (SRAM), dynamic random access memory (DRAM), synchronous DRAM (SDRAM), read-only memory (ROM), a combination thereof, or the like. In an embodiment, the memory may include ROM for use at boot-up, and DRAM for program and data storage for use while executing programs.

The mass storage device may comprise any type of non-transitory storage device configured to store data, programs, and other information and to make the data, programs, and other information accessible via the bus. The mass storage device may comprise, for example, one or more of a solid state drive, hard disk drive, a magnetic disk drive, an optical disk drive, or the like.

The video adapter and the I/O interface provide interfaces to couple external input and output devices to the processing unit. As illustrated, examples of input and output devices include the display coupled to the video adapter and the mouse/keyboard/printer coupled to the I/O interface. Other devices may be coupled to the processing unit, and additional or fewer interface cards may be utilized. For example, a serial interface such as Universal Serial Bus (USB) (not shown) may be used to provide an interface for a printer.

The processing unit also includes one or more network interfaces, which may comprise wired links, such as an Ethernet cable or the like, and/or wireless links to access nodes or different networks. The network interface allows the processing unit to communicate with remote units via the networks. For example, the network interface may provide wireless communication via one or more transmitters/transmit antennas and one or more receivers/receive antennas. In an embodiment, the processing unit is coupled to a local-area network or a wide-area network for data processing and communications with remote devices, such as other processing units, the Internet, remote storage facilities, or the like.

The following references are related to subject matter of the present application. Each of these references is hereby incorporated herein by reference in its entirety: U.S. patent application Ser. No. 13/808,229 filed on Jan. 3, 2013, entitled "Marking System for Computer-Aided Detection of Breast Abnormalities;" U.S. patent application Ser. No. 13/695,369 filed on Oct. 30, 2012, entitled "Spiculated Malignant Mass Detection and Classification in Radiographic Images;" U.S. patent application Ser. No. 13/695,351 filed on Oct. 30, 2012, entitled "Probability Density Function Estimation;" U.S. patent application Ser. No. 13/695,347 filed on Oct. 30, 2012, entitled "Microcalcification Detection Classification in Radiographic Images;" U.S. patent application Ser. No. 13/168,614 filed on Jun. 24, 2011, entitled "Breast Skin Line Detection in Radiographic Images;" U.S. patent application Ser. No. 13/168,588 filed on Jun. 24, 2011, entitled "Breast Segmentation in Radiographic Images;" and U.S. patent application Ser. No. 10/996,595 filed on Nov. 23, 2004, entitled "CAD Medical Imaging System, Components, and Method of Operation."

While this invention has been described with reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. A method for breast density computation comprising:
   performing, by a processor, breast segmentation on a mammographic image to obtain breast and pectoral muscle segmentation maps;
   performing breast thickness correction on the mammographic image to obtain a flattened breast image; and
   computing a breast density measurement in accordance with the breast and pectoral muscle segmentation maps and the flattened breast image, wherein computing the breast density measurement in accordance with the breast and pectoral muscle segmentation maps and the flattened breast image comprises:
      performing breast density estimation to obtain an initial density map;
      performing breast density segmentation on the initial density map to obtain a final density map; and
      computing the breast density measurement in accordance with the final density map,
   wherein performing breast density segmentation on the initial density map to obtain the final density map comprises:
      refining the initial density map to obtain a refined density map, wherein refining the initial density map includes extracting fatty tissue from the initial density map and filling in holes in parenchyma regions of the initial density map;
      segmenting the flattened breast image to obtain a flattened-image density map; and
      combining the flattened-image density map with the refined density map to obtain the final density map.

2. The method of claim 1, wherein the breast and pectoral muscle segmentation maps classify pixels in the mammographic image as representing breast tissue, pectoral tissue, or background.

3. The method of claim 2, wherein the breast and pectoral muscle segmentation maps indicate a first boundary line in the mammographic image, the first boundary line separating pixels representing pectoralis tissue from pixels representing breast tissue.

4. The method of claim 3, wherein the breast and pectoral muscle segmentation maps indicate a second boundary line in the mammographic image, the second boundary line separating pixels representing a breast tissue from pixels representing background.

5. The method of claim 4, wherein performing breast thickness correction on the mammographic image to obtain the flattened breast image comprises:
   computing an estimate of fatty tissue as a function of distance from the second boundary line; and
   subtracting the estimate of fatty tissue from the mammographic image to obtain the flattened image.

6. The method of claim 1, further comprising performing breast density estimation to obtain the initial density map by:
   filtering the mammographic image using multiple scales to obtain filtered outputs, wherein each filtered output corresponds to a different scale;
   analyzing the filtered outputs to obtain signals within corresponding regions of interest (ROI), wherein each corresponding ROI is a function of the scale used to obtain the filtered output; and
   combining the signals in accordance with a weighted value to generate the initial density map.

7. The method of claim 6, wherein filtering the mammographic image using multiple scales to obtain filtered outputs comprises:
   filtering the mammographic image in a spatial domain.

8. The method of claim 6, wherein filtering the mammographic image using multiple scales to obtain filtered outputs comprises:
   filtering the mammographic image in a frequency domain.

9. The method of claim 6, wherein filtering the mammographic image using multiple scales to obtain filtered outputs comprises:
   filtering the mammographic image in a joint spatial frequency domain.

10. The method of claim 1, wherein combining the flattened-image density map with the refined density map to obtain the final density map comprises:
    taking a logical AND of the flattened-image density map and the refined density map to generate the final density map.

11. The method of claim 1, wherein computing the breast density measurement in accordance with the final density map comprises:
    calculating a dense area in accordance with the final density map;
    calculating a breast area in accordance with a breast segmentation map; and
    calculating the breast density measurement in accordance with the dense area and the breast area.

12. The method of claim 11, wherein calculating the breast density measurement in accordance with the dense area and the breast area comprises:
    dividing the dense area by the breast area to obtain a ratio; and
    multiplying the ratio by one hundred percent to obtain the breast density measurement.

13. An apparatus comprising:
a processor; and
a non-transitory computer readable storage medium storing programming for execution by the processor, the programming including instructions to:
perform breast segmentation on a mammographic image to obtain breast and pectoral muscle segmentation maps;
perform breast thickness correction on the mammographic image to obtain a flattened breast image; and
compute a breast density measurement in accordance with the breast and pectoral muscle segmentation maps and the flattened breast image, wherein computing the breast density measurement in accordance with the breast and pectoral muscle segmentation maps and the flattened breast image comprises:
performing breast density estimation to obtain an initial density map;
performing breast density segmentation on the initial density map to obtain a final density map; and
computing the breast density measurement in accordance with the final density map,
wherein performing breast density segmentation on the initial density map to obtain the final density map comprises:
refining the initial density map to obtain a refined density map, wherein refining the initial density map includes extracting fatty tissue from the initial density map and filling in holes in parenchyma regions of the initial density map;
segmenting the flattened breast image to obtain a flattened-image density map; and
combining the flattened-image density map with the refined density map to obtain the final density map.

14. The apparatus of claim 13, wherein the breast and pectoral muscle segmentation maps classify pixels in the mammographic image as representing breast tissue, pectoral tissue, or background.

* * * * *